(12) United States Patent
Schulze

(10) Patent No.: US 6,185,989 B1
(45) Date of Patent: Feb. 13, 2001

(54) DEVICE FOR DYNAMIC MEASUREMENT OF THE SURFACE TENSION OF A LIQUID

(75) Inventor: Lothar Schulze, Dresden (DE)

(73) Assignee: Sita Messtechnik GmbH, Dresden (DE)

(*) Notice: Under 35 U.S.C. 154(b), the term of this patent shall be extended for 0 days.

(21) Appl. No.: 09/242,203

(22) PCT Filed: May 24, 1997

(86) PCT No.: PCT/DE97/01085

§ 371 Date: Feb. 11, 1999

§ 102(e) Date: Feb. 11, 1999

(87) PCT Pub. No.: WO97/46863

PCT Pub. Date: Dec. 11, 1997

(30) Foreign Application Priority Data

May 31, 1996 (DE) .............................. 296 09 646

(51) Int. Cl.⁷ .................................................. G01N 13/02
(52) U.S. Cl. ........................................ 73/64.51; 73/64.48
(58) Field of Search ............................... 73/64.48, 64.51, 73/37

(56) References Cited

U.S. PATENT DOCUMENTS

| 3,765,227 | * | 10/1973 | Campbell et al. | ..................... 73/64.4 |
| 3,992,662 | * | 11/1976 | Koepnick et al. | ..................... 324/30 |
| 4,416,148 | * | 11/1983 | Klus et al. | ............................ 73/64.4 |
| 4,527,421 | * | 7/1985 | Miller, Jr. | .............................. 73/64.4 |
| 4,831,565 | * | 5/1989 | Woodward | ..................... 364/571.01 |
| 5,099,679 | * | 3/1992 | Muelimann et al. | ................ 73/19.06 |
| 5,587,527 | * | 12/1996 | Radford et al. | .......................... 73/439 |
| 6,085,577 | * | 7/2000 | Christensen et al. | ................ 73/64.51 |

FOREIGN PATENT DOCUMENTS

| 2915956 | 11/1980 | (DE) . |
| 4112417 | 10/1992 | (DE) . |
| 4303133 | 8/1994 | (DE) . |
| 4423720 | 2/1996 | (DE) . |
| 0 149 500 | 7/1985 | (EP) . |
| WO 96/18877 | 6/1996 | (WO) . |

OTHER PUBLICATIONS

User Handbook of the company Krüss GmbH, Hamburg, Germany, regarding pressure tension meter of 1995.

* cited by examiner

Primary Examiner—Hezron Williams
Assistant Examiner—Charles Garber
(74) Attorney, Agent, or Firm—Collard & Roe, P.C.

(57) ABSTRACT

The invention relates to a device for dynamic measurement of the surface tension of a liquid by the bubble pressure process. The device is characterized by a moving measuring device with a flexible lead, conveying at least compressed air, to a sensor head which releases bubbles and can be immersed in the measuring liquid. The moving measuring device has an input keyboard for different operating modes, a display for monitoring the measuring modes and display of the measurement results, a volume flow source for generating the gas pressure, a pressure sensor for detecting the quality of gaseous bubbles, a microprocessor for measuring and evaluating the measurement results and an internal current supply for all power consumers.

5 Claims, 3 Drawing Sheets

DEVICE FOR DYNAMIC MEASUREMENT OF THE SURFACE TENSION OF A LIQUID

BACKGROUND OF THE INVENTION

1. Field of the Invention

The present invention relates to a device for dynamic measurement of the surface tension at boundary surfaces between liquids and gasses according to the method of evaluation of the maximum bubble pressure.

2. Description of the Related Art

A device of this type and a measurement process for this is described in greater detail in, for example, EP 0 149 500 A2.

For the theory and for further understanding of the measurement method, reference is made to the company publication: Blasendrucktensiometer BP2, Benutzerhandbuch, Krüss GmbH, Hamburg 1995.

The mentioned devices are suitable for stationary laboratory testing of liquids. Very high demands are made on the measurement conditions. Thus, for example, the state of fullness or, rather, the immersion depth of the capillary in the measurement liquid must be adjusted with millimeter precision with the aid of a sinking device, in which process a height adjustment up to the "jumping" of the liquid onto the capillary must first be undertaken manually and with very great care. The installation location is to be chosen with great care, since, for example, vibrations due to personnel walking by or drafts ensure a serious adulteration of the measurement results. Also, the measurement apparatus is to be carefully aligned. By reason of the demanding design of the measurement place and the high weight of about 20 kg, mobile application is prohibited. A further reason for the fixed design of the measurement place is that for the generation of bubbles relatively high pressures are required, for which, in turn, large external pressure-gas producers must be available and, obviously, an electrical connection must be present. The regulation of the bubble formation and/or bubble frequency takes place in a demanding manner by means of analog valves. The evaluation can take place only on a personal computer.

Furthermore, devices are known that for the purpose of continuous measurements are in constant contact with a particular liquid to be tested (DE 41 12 417 A1, DE 43 03 133 A1), and which are very expensive. An external air compressor, two compressed-air hoses, two valves, and two different precision capillaries, immersed to exactly the same depth, are necessary for the generation of the gas bubbles, as well as a pressure-difference gauge at the capillary feeds. The evaluation takes place on a personal computer. Disturbances, caused by a bubble break-off at one of the capillaries, makes an evaluation difficult.

In all known devices the pressure or rather the pressure difference between two capillaries is measured as an absolute value, for which purpose relatively cost-intensive pressure sensors with a very precise calibration are required.

Finally, from DE 44 23 720 C1 is known a generically different device for measuring the surface tension of preferably molten metals, with one capillary for the gas supply, which capillary is conducted for example vertically through the bottom of a crucible receiving the molten metal and terminates at a nozzle for the formation of the gas bubbles. With knowledge of the surface tension of cast iron, by means of this device conclusions can be made regarding the graphite morphology of the carbon contained in the cast iron, and the sulfur content of the pig iron or even the refinement processing of aluminum-silicon alloys can be judged.

It is a matter here of an elaborate apparatus to be operated in a stationary manner, with which apparatus the frequency of the gas bubbles emerging from the nozzle into the molten cast iron is determined. The relatively long capillary with an inner diameter of only 0.7 to 1.5 mm causes a considerable flow resistance for the gas the thus necessitates a high expenditure of energy during the measuring process. Beyond that, during the operation the moistening characteristics and the inner diameter of the capillary are altered by the measurement melt penetrating more or less into the capillary, and thus the measurement parameters are also altered uncontrollably, which leads, finally, to uncertain measurement results. Moreover, after every measurement a careful purging of the capillary or, better, its replacement is necessary. Both of these are time-consuming and expensive.

SUMMARY OF THE INVENTION

The task of the invention is to create a compact device for a nearly universal, simple, reliable and low-maintenance use. The device should make possible good measurement precision even with relatively large fill-state tolerance of the liquid in the container, and have a low power usage, a low weight, and greatly reduced production costs. In particular, the carrying out of its application should be possible in a mobile manner, whereby the constant sending in of test samples to a laboratory is just as dispensable as with an apparatus that is bound to one installation. Further, it should be possible to measure even the smallest amounts of liquid.

The task is accomplished through the characterizing features of the first claim. Advantageous further developments are specified in the dependent claims.

With the apparatus according to the invention, industry is given a small, light measurement device that is not dependent on an electrical means or air pressure, in short is mobile, that is relatively robust and simple to operate, and nevertheless is capable of delivering good measurement results with low acquisition cost and universal application. The measurement apparatus is operated via an input keypad and has different operating modes. The selected operating mode and the measurement results and/or error messages can be read off from a display. An internal volumetric-flow source generates the necessary gas pressure, the quality of the gas bubbles is measured by an internal pressure sensor, and the evaluation takes place by means of a microprocessor. An internal power supply supplies all power consumers independently of an electrical means as desired. It consists of a 110/220-volt power unit and/or a rechargeable or expendable battery.

Used advantageously as a volumetric-flow source is a controllable low-voltage membrane pump that is capable of building up a sufficiently constant gas pressure. When the nozzle according to the invention is used, the necessary gas pressure amounts to only about $1/10$ of the pressure in the standard devices.

For the pressure sensor is used, according to an especially preferred implementation, a sound-pressure transducer, namely a mini-microphone. This is cost-effective and delivers at its output the first derivative of the measured bubble pressure, thus a measurement signal that is independent of the immersion depth of the nozzle.

The measurement apparatus has four selectable operating modes, namely a calibration mode, a first measurement mode for surface-tension measurement with a constant, selected bubble frequency, a second measurement mode for surface-tension measurement with automatic bubble-frequency through-flow, and a purging mode, as well as an additional error mode.

According to an advantageous implementation, a nozzle directed toward the surface of the liquid is installed in the sensor head, the length of which nozzle is very short in relation to the nozzle opening. By this means an undisturbed bubble break-off is produced in the direction of the lifting force of the bubbles, which contributes to the precision of measurement. Moreover, the nozzle shape makes a purging considerably easier, and the required gas pressure for the production of gas bubbles in the measurement liquid sinks by an order of magnitude, which is of particular significance for a battery-operated, handheld measurement apparatus.

Obviously, instead of the measurement nozzle a capillary can be arranged in the sensor head (1) for generating the gas bubbles.

Since the surface tension becomes lower with a rising temperature, in a further configuration of the invention provision is additionally made in the sensor head for a temperature sensor for the evaluation of the measurement results.

In addition, in the region of the measurement liquid a conductivity sensor can also be arranged in the sensor head, in order to measure the conductivity of the measurement liquid simultaneously with the measurement of the surface tension.

A fill-state sensor in the sensor head is indispensable if a static pressure sensor is employed.

For especially exact measurements, it is of advantage to fasten the sensor head (1) into a holder.

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the views.

DETAILED DESCRIPTION OF THE PREFERRED EMBODIMENT

Figure 1:
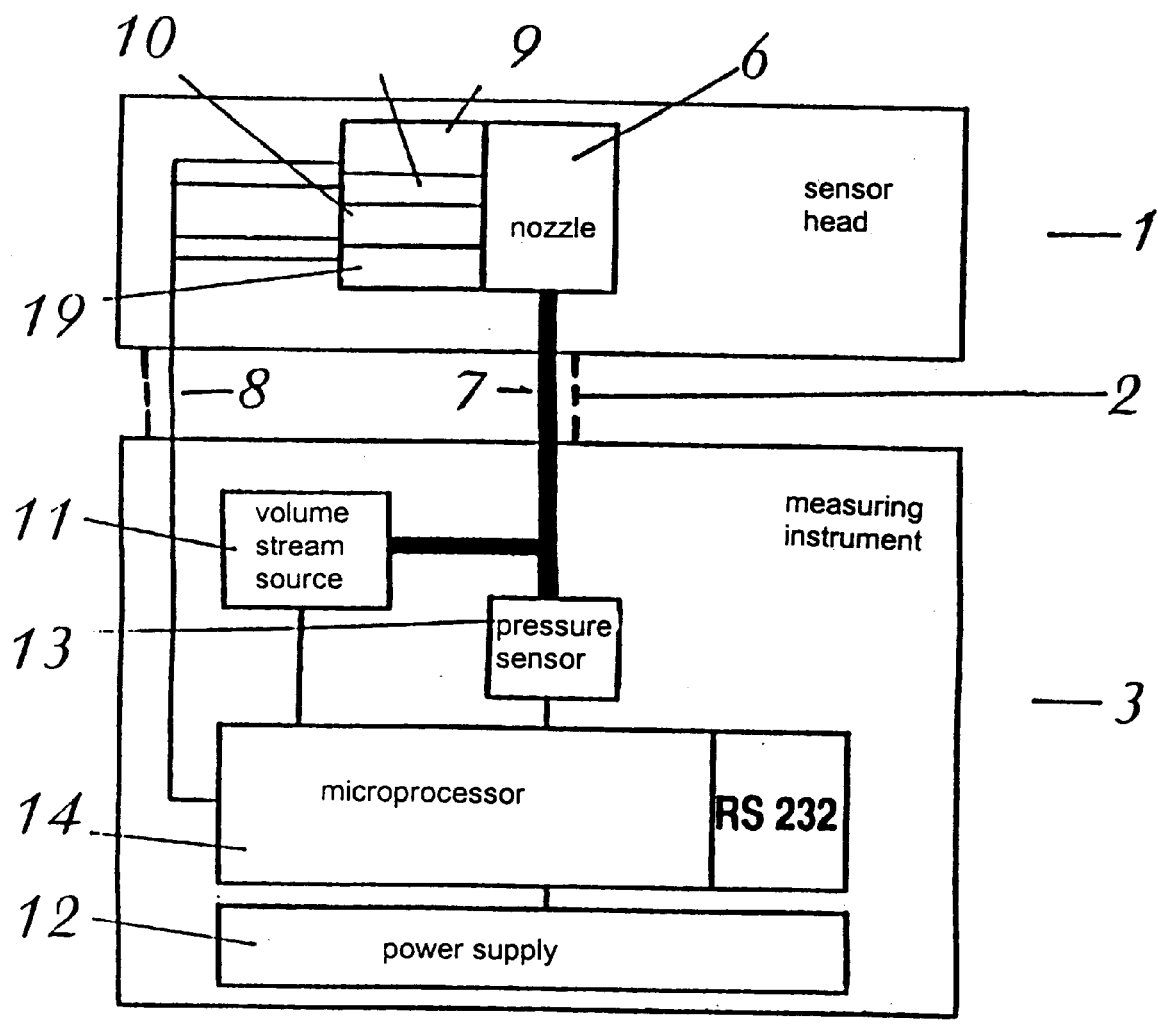
FIG. 1 shows: the functional structure of a handheld measurement apparatus
Figure 2:
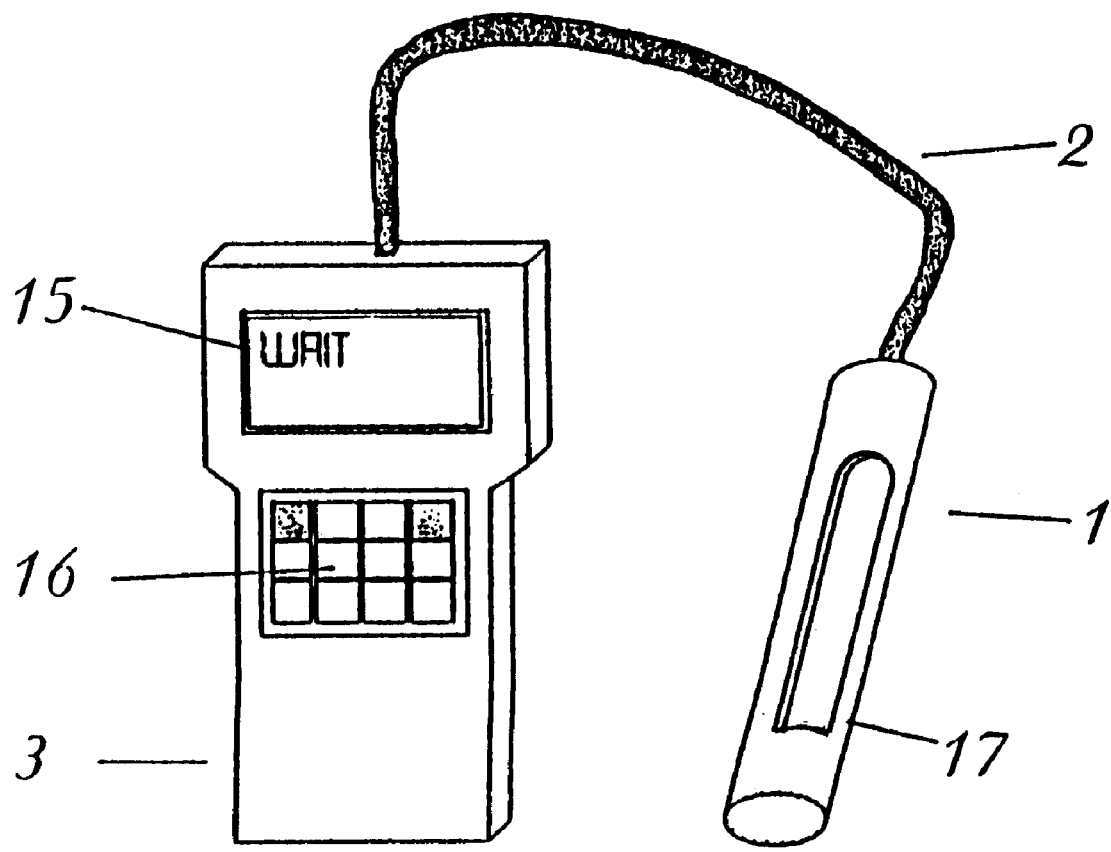
FIG. 2 shows: a structural implementation of the collective apparatus
Figure 3:
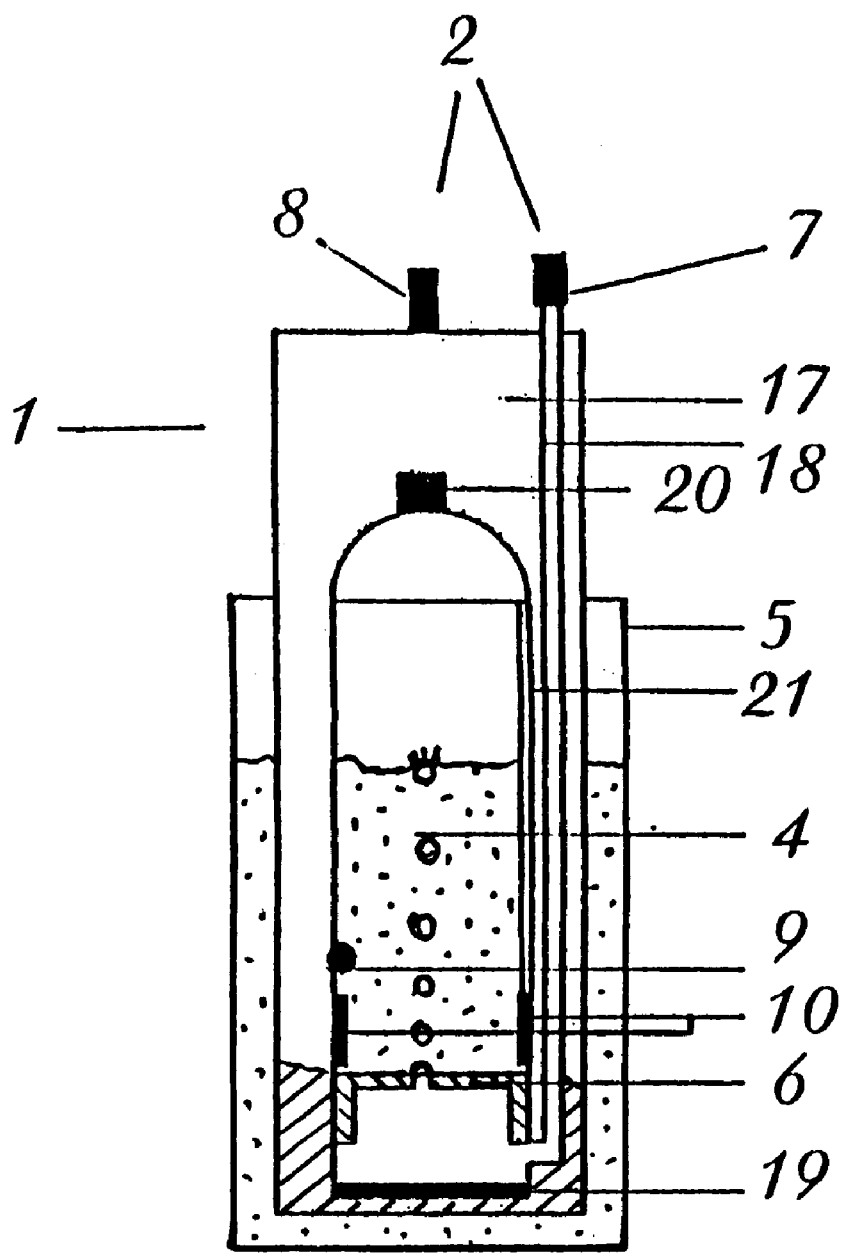
FIG. 3 shows: the structure of a sensor head according to the invention

A sensor head 1 is connected to a handheld measurement apparatus 3 via a flexible supply duct 2. In the sensor head 1 (still to be described in greater detail), into which a measurement liquid 4 can flow upon the immersion of the sensor head 1 into measurement vessel 5, is situated a nozzle 6, through which the bubbles can be forced into the measurement liquid 4 via the supply duct 2. The supply duct 2 consists of a flexible hose 7 end, if necessary, of current-conducting, insulated stranded wires 8 for supplying additional sensors 9, 10, 19, 20, 21.

In the housing of the handheld measurement apparatus 3 is accommodated as a volumetric-flow source a uniformly-operating, controllable membrane pump with a power consumption of fewer than 5 watts. The membrane pump is connected to a power supply 12, a 110/220-volt power unit and/or a storage cell, or rather, a battery. Via a T-piece in the hose 7 the air pressure built up by the membrane pump reaches a pressure sensor 13, advantageously a sound-pressure transducer, as well as a nozzle 6, where a bubble develops. The sound-pressure transducer converts the static pressure portion of the bubble pressure into a measurement signal differentiated according to time, whereby the measurement becomes independent of the fill state of the measurement vessel, and/or independent of the depth of immersion of the sensor head 1 in the measurement solution 4, which is an essential prerequisite for a handheld measurement apparatus 3 that is to be operated in an uncomplicated manner. Also, a sound-pressure transducer is significantly more cost-effective than a conventionally-applied pressure sensor that must be calibrated in an elaborate manner. Through integration over time in a microprocessor 14, the bubble pressure and thus the surface tension of the liquid 4 can be easily determined. Moreover, the measurement magnitudes, bubble frequency, temperature and, if necessary, the conductivity of the measurement liquid 4 can be displayed on an LCD display 15 on the handheld measurement apparatus 3 and stored in the microprocessor 14, along with the data and time of the measurement. Via a computer interface, e.g. RS 232, a transmission to an external personal computer of all measurement values for representation and further processing is possible as an option. The operating of the handheld measurement apparatus 3 takes place by means of an input keypad 16.

The sensor head 1 has a sensor housing 17, in whose lower region the nozzle 6 is arranged. The nozzle 6 has a very long length in relation to the nozzle opening, whereby the disturbing effect of capillary forces dependent of boundary-surface tension, as occur with measurement capillaries, remains essentially without influence. Also, through this means a purging of the nozzle 6 is made considerably easier and the necessary gas pressure significantly lessened.

The nozzle 6 is directed towards the surface of the measurement liquid 4, so that the break-off direction corresponds to the natural direction of buoyancy of the gas bubble, whereby measurement errors are reduced. Serving the gas feed is a channel 18 passing through the sensor housing 17, which channel has a mouth underneath the nozzle 6.

Further, in the region of the moistening by the measurement liquid 4 a temperature sensor 9 is arranged and connected to the microprocessor 14 in the handheld measurement apparatus 3 via a stranded wire 8 guided through the supply duct 2. The registering of the temperature and, if need be, a temperature compensation is important for reasons of the essentially linear dependence of the surface tension on temperature, because with the handheld measurement apparatus 3 measurement liquids 4 between 10° C. and 90° C. are to be diagnosed.

On the bottom of the sensor housing 17, still lower than the mouth of the channel 18, is advantageously arranged a ceramic moisture or conductivity sensor 19. In the space between this sensor 19 and the nozzle opening there is normally no measurement liquid 4. The sensor 19 monitors a possible penetration of measurement liquid 4 into the nozzle 6 and if this is the case gives a signal to the microprocessor 14.

Furthermore, above the nozzle 6 can be situated a conductivity sensor 10, preferably capacitive, whose electrodes are attached to the inside wall of the sensor housing 17. Applied to the electrodes, in a known manner, is an alternating voltage. The capacitor consisting of the electrodes and the measurement liquid 4 located between them produces an electrical impedance, from which impedance measurement values regarding the concentration of, for example, cleansing agents in the measurement liquid 4 can be ascertained. With this, the possibility of determining at the same time both the surface tension and the conductivity of the measurement liquid 4 is created.

Finally, fill-state sensors 20, 21 can be accommodated in the sensor housing 17, which sensors signal the level of the measurement liquid 4 in the sensor head 1. Although the measurement is largely independent of the liquid level, naturally sufficient liquid 4 must be present to develop a homogeneous bubble stream.

First Measurement Mode

The handheld measurement apparatus has four operating modes and one error mode, which are selectable via the keypad 16.

1. Calibration Mode

In the calibration mode, a system check takes place first and then the calibration of the handheld measurement apparatus 3 to the surface tension of a know liquid, e.g. water or alcohol.

2.

In measurement mode 1 the surface-tension measurement takes place with the bubbles emerging at a constant frequency; preferably, bubble frequencies of 1 Hz to 10 Hz are selectable. However, wider frequency ranges are also possible.

3. Second Measurement Mode

In second measurement mode the surface-tension measurement takes place with an automatic frequency throughflow of the bubble emergence from 1 Hz to 10 Hz. Wider frequency ranges are also possible.

4. Purging Mode

A purging of the nozzle 6 takes place with the full volumetric-flow power of the volumetric-flow source 11.

5. Error Mode

The handheld measurement apparatus 3 automatically recognizes errors occurring in operation and handling, as well as during measurement, so that erroneous measurements are excluded to the greatest degree. The errors are indicated on the LCD display 15. Thus, measurement liquid 4 penetrating the nozzle 6 is registered and indicated. Furthermore, the turning off of the handheld measurement apparatus 3 by means of an OFF key is only possible if the sensor head 1 has been removed from the measurement liquid 4. By this means, for all practical purposes the measurement liquid is prevented from getting into the nozzle 6. Further, the exceeding of or falling below the measurement region of the surface tension, which region preferably lies between 15 and 80 mN/m, the temperature of the measurement liquid 4 between 0° C. and 100° C., and the ambient temperature are indicated.

Accordingly, while only one embodiment of the present invention has been shown and described, it is obvious that many changes and modifications may be made thereunto without departing from the spirit and scope of the invention.

One field of application is, for example, the diagnosis of surfactant-containing suds or rinse waters, another is the quality assurance of surfactant-containing inks, pigments, cleansing media, or wiper fluids. Among other things, with the device according to the invention a very good diagnosis of pesticide, photochemical, and pharmaceutical solutions is possible. Additional fields of application open up in the semiconductor, metal-processing, and textile industries.

What is claimed is:

1. A mobile device for dynamically measuring the surface tension of a liquid using a bubble pressure method comprising:

a hand held measuring instrument comprising:
    a micro processor for controlling and processing measurements;
    a display screen connected to said microprocessor for displaying measured results;
    an input keyboard connected to said display screen for selecting modes of measurement, calibration and cleaning of the surface tension;
    a volume stream source connected to said microprocessor for producing the bubbles;
    a pressure sensor connected to said microprocessor for detecting measurement signals; and
    a power supply connected to said microprocessor; and
a sensor head having a nozzle for releasing bubbles into the liquid, said sensor head bring connected to said measuring instrument by a flexible feed line that feeds pressurized gas from said volume stream source to said sensor head.

2. The device according to claim 1, wherein said microprocessor is equipped with a first measurement mode for measuring the surface tension with constant, selectable bubble frequency and a second measurement mode for measuring the surface tension with an automatic bubble frequency cycle.

3. The device according to claim 1, wherein said pressure sensor is designed as a sound pressure converter.

4. The device according to claim 1, further comprising a filling level sensor in said sensor head.

5. The device according to claim 1, wherein said sensor head is secured with a holding device.

* * * * *